United States Patent [19]

Hadford et al.

[11] Patent Number: 4,675,004
[45] Date of Patent: Jun. 23, 1987

[54] DUAL-LUMEN FISTULA NEEDLE

[75] Inventors: Raymond L. Hadford, Snohomish County; Wayne E. Quinton, King County, both of Wash.

[73] Assignee: Quinton Instrument Company, Seattle, Wash.

[21] Appl. No.: 723,802

[22] Filed: Apr. 16, 1985

[51] Int. Cl.⁴ .............................................. A61M 5/00
[52] U.S. Cl. .......................................... 604/44; 604/4; 604/272
[58] Field of Search ...................... 604/44, 43, 42, 264, 604/272, 4, 220

[56] References Cited

U.S. PATENT DOCUMENTS

| | | | |
|---|---|---|---|
| 2,175,726 | 10/1939 | Gebauer | 604/102 X |
| 4,073,297 | 2/1978 | Kopp | 604/44 |
| 4,098,275 | 7/1978 | Consalvo | 604/44 |
| 4,134,402 | 1/1979 | Mahurkar | 604/44 |
| 4,203,436 | 5/1980 | Grimsrud | 604/44 |
| 4,543,087 | 9/1985 | Sommercorn et al. | 604/43 |
| 4,583,968 | 4/1986 | Mahurkar | |

FOREIGN PATENT DOCUMENTS 8404043 10/1984 Int'l Pat. Institute ................ 604/44

Primary Examiner—Stephen C. Pellegrino
Attorney, Agent, or Firm—Seed and Berry

[57] ABSTRACT

A dual-lumen fistula needle for use in hemodialysis treatment. The needle has a gently tapered neck and is divided into arterial and venous lumens by a center septum which is bonded in place. The septum is formed so that the lumens have substantially equal cross sections substantially throughout the length of the needle to promote equal flow rates in the lumens. The diameter of the needle at the tip is similar to that of single-lumen needles in order to reduce discomfort on insertion.

13 Claims, 5 Drawing Figures

DUAL-LUMEN FISTULA NEEDLE

DESCRIPTION

1. Technical Field

The invention relates to a needle for hemodialysis treatment. Specifically, the invention relates to a dual-lumen needle for use in continuous flow hemodialysis.

2. Background Art

Hemodialysis treatments involve drawing blood from a patient, treating the blood, and returning the blood to the patient. Typically, the drawn or arterial blood is returned to the same vein as the treated or venous blood. This can be accomplished by introducing two separate needles, or lumens, into a vein or fistula a distance apart. The arterial lumen is placed upstream of the venous lumen so that only untreated or arterial blood is drawn into the hemodialysis unit.

An obvious disadvantage of this procedure is that the patient must be punctured twice for each treatment. This is especially disadvantageous when the needles are inserted into a fistula to access the patient's blood. A fistula is a surgically created shunt between an artery and a vein. Since the arterial pressure is usually much greater than the venous pressure, the vein swells, providing a good access for hemodialysis needles. The fistula, being an abnormally presurized vein, is particularly susceptible to collapse or failure due to punctures. It is highly preferred, therefore, to minimize the number of punctures to the fistula to improve its useful life. To reduce the number of punctures per treatment by one-half, double-lumen hemodialyis needles, or catheters, have been developed. These catheters, such as the catheter disclosed by Mahurkar in U.S. Pat. No. 4,134,402, provide a single needle with two contiguous lumens. Thus the patient need only be punctured once for each treatment, since a single needle contains both the arterial or intake lumen and the venous or return lumen. Devices like the Mahurkar catheter are extremely difficult to manufacture. Typically, a relatively thin needle, having a D-shaped cross section, is inserted into a larger cylindrical needle. The inside surface of the cylindrical needle has a radius of curvature which is slightly larger than the curvature of the thinner needle. The thinner needle extends from the cylindrical needle and divides the cylindrical needle into intake and return lumens. The needles are then swaged to form a tip. This structure has a number of limitations which have limited the usefulness of Mahurkar catheters. For example, the cross-sectional discontinuity between the portion of the catheter where the intake and return lumens are contiguous and where the return lumen extends past the intake lumen can cause discomfort to the patient when the catheter is inserted.

DISCLOSURE OF THE INVENTION

It is an object of the invention to provide a dual-lumen fistula needle which is easily manufacturable.

It is also an object of the invention to provide a dual-lumen fistula needle which reduces trauma to the patient on insertion.

It is a further object of the invention to maintain substantially equal blood flow rates in the intake and return lumens.

The invention achieves these objectives by providing a dual-lumen needle having a cylindrical shaft and a gently tapered neck which ends in a penetrating tip. The tip has a diameter which is similar to that of single-lumen needles and gradually tapers through the neck portion to the shaft diameter without any severe discontinuities. Thus, the discomfort associated with insertion of the invention is similar to the discomfort associated with single-lumen needles.

A separately formed center septum is bonded into place within the needle and divides the needle into a blood intake lumen and a blood return lumen. A blood inlet, which is formed on the neck portion at the beginning of the taper, communicates with the intake lumen to form an arterial flow path. The end of the penetrating tip forms a blood outlet which communicates with the return lumen to form a venous flow path. The septum conforms to the changing inner surface of the needle so that the cross-sectional area of both the intake lumen and return lumen is substantially equal throughout the length of the needle. Thus, the rate of blood flow in the return lumen is substantially equal to the rate of blood flow in the intake lumen. It is extremely important to maintain equal flow rates and pressures within the lumens to avoid aeration of the blood in the hemodialysis unit. Furthermore, bonding a separately formed center septum into the shaft significantly facilitates manufacturing the needle.

The needle can be manufactured with a connector portion and stabilizer tubes so that the needle can be used with continuous-flow hemodialysis units. The connector portion has one end adapted to connect with the intake lumen and the return lumen at the base of the needle. The other end of the connector portion is adapted to accept two stabilizer tubes having standard Luer ends connected thereto.

Additionally, the needle can be provided with a smooth inner surface to reduce turbulence in the blood flow within the needle.

BEST MODE FOR CARRYING OUT THE INVENTION

Figure 1:
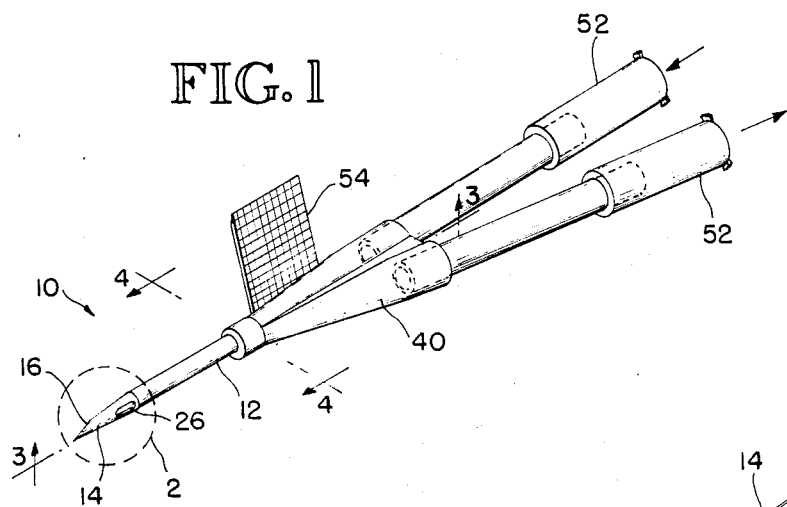
FIG. 1 is an isometric view of a double-lumen needle in accordance with the present invention, including a connector portion and stabilizer tubes for use with a conventional hemodialysis unit.
Figure 2:
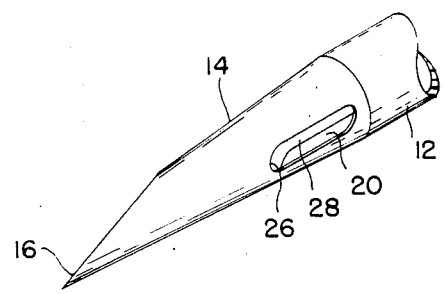
FIG. 2 is an enlarged isometric view of the neck portion illustrating the blood inlet and a portion of the center septum.
Figure 3:
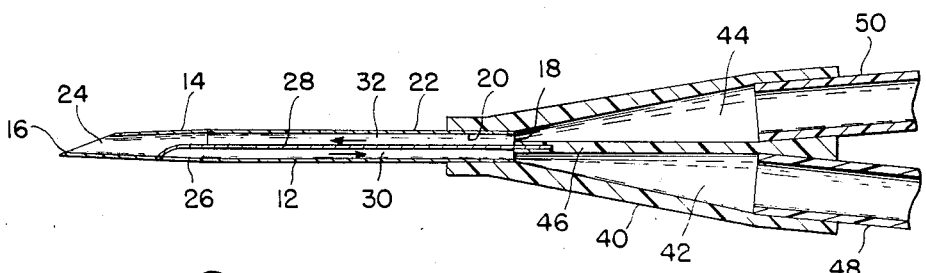
FIG. 3 is a partial, sectional side elevational view of the needle looking generally in the direction of arrows 3—3 of FIG. 1.

In FIG. 1, a dual-lumen fistula needle, or needle, in accordance with the present invention, is generally indicated at reference numeral 10. The needle has a longitudinally extending cylindrical shaft 12, which tapers to form a neck 14, and a penetrating tip 16 at the distal end of the needle. As seen in FIG. 3, the shaft 12 also has a base 18, an inner surface 20, and an outer surface 22. The inner surface defines a fluid conduit for the shaft and has a diameter which corresponds to the diameter of the outer surface such that the wall thickness of the needle is substantially constant. The shaft 12 is symmetrically tapered about the longitudinal axis thereof to form the neck 14. The penetrating tip 16 is provided with a blood outlet 24 which traverses the longitudinal axis. It is preferred to form the neck by swaging the shaft in a series of steps so that the outer surface is smooth and the taper gradual. Thus, incremental discontinuities between various sections of the needle are minimal so that the patient is subjected to a minimum of discomfort when the needle is inserted into a vein or fistula. A blood inlet 26 is provided on the neck 14.

Figure 4:
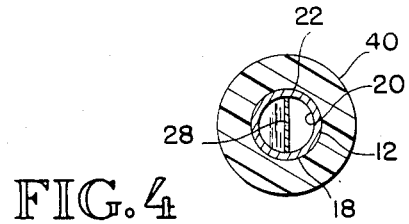
FIG. 4 is an enlarged sectional view of the needle looking in the general direction of arrows 4—4 of FIG. 1.

A center septum 28 divides the fluid conduit into a blood intake lumen 30 and a blood return lumen 32. The septum is manufactured separately from the shaft and is inserted into the shaft and bonded in place. The septum has a substantially straight, rectangular portion and a tapered portion which is bent out of a plane defined by the rectangular portion. As seen in FIG. 4, the width of the septum conforms to the shape of the inner surface 20 so that blood flowing into the intake lumen 30 through the blood inlet 26 cannot mix with blood exiting the return lumen 32 through the blood outlet 24. The septum is inserted into the needle through the base 18. The width of the septum is chosen so that the septum fits tightly within the needle. To facilitate insertion of the septum through the base, the shaft is compressed slightly to elastically expand the diameter of the shaft along a diameter perpendicular to the direction of compression. The compression is released after the septum has been inserted so that the shaft returns to its rigid cylindrical shape, gripping the septum tightly. The bonding agent is deposited to the septum through the blood inlet 26. Capillary action draws the adhesive, or bonding agent, along the edges of the septum and the inner surface 20 of the shaft 12. A number of adhesives, such as cyanoacrylate, have a sufficiently low viscosity so that capillary action can bond the septum in place.

The placement of the septum within the shaft and the geometry of the taper and the size of the blood inlet and blood outlet are critical in maintaining substantially similar flow rates in both the intake lumen and return lumen. If the pressures and flow rates in the lumens are not equal, aeration of the blood can result in the drip chamber of hemodialysis units. It is preferred to begin tapering the shaft 12 to form the neck 14 near the blood inlet 26 and continue the taper of the shaft 12 to the penetrating tip 16 uniformly. This causes the intake lumen 30 and the return lumen 32 to have substantially equal cross sections throughout the length of the needle. The areas of the blood outlet 24 and the blood inlet 26 are equal to or larger than the cross-sectional area of the lumens, so the lumen cross sections and lengths determine the flow rates. Since the cross-sectional areas and lengths of the lumens are substantially equal, the flow rates for the intake and return lumens are substantially the same. Other methods for equalizing the flow rates within the lumens can be substituted.

The orientation of the blood inlet 26 encourages blood to enter the intake lumen transverse to the longitudinal axis of the shaft, whereas the orientation of the blood outlet 24 encourages blood to exit the blood return lumen 32 longitudinally. Thus, mixing or recirculation of the arterial blood with the venous blood is virtually eliminated.

Various arrangements can be used to connect the needle 10 to standard hemodialysis units. The needle can be provided with a connector portion 40 wherein one end of the connector portion engages the base 18 of the shaft 12 and a portion of the outer surface 22 of the shaft. The connector portion has an arterial chamber 42 and a venous chamber 44 separated by a wall 46. The center septum 28 extends beyond the base 18 of the shaft 12 to engage the wall so that the arterial chamber defines a flow path from the intake lumen 30 and the venous chamber defines a flow path to the return lumen 32. An arterial stabilizer tube 48 is connected to the arterial chamber 42 of the connector portion to further extend the arterial flow path. Similarly, a venous stabilizer tube 50 is connected to the venous chamber 44 of the connector portion to extend the venous flow path. Both the arterial and venous stabilizer tubes are provided with standard Luer ends 52 so that the needle 10 may be used with typical hemodialysis equipment.

A mast 54 can be provided on the connector portion 40 to facilitate taping the needle 10 to the patient.

Figure 5:
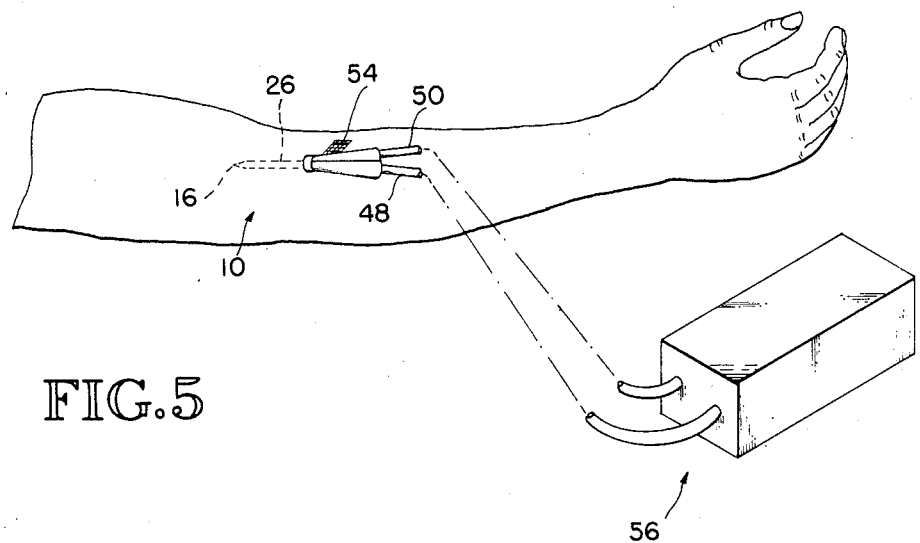
FIG. 5 is an isometric view showing a patient connected to a dialysis machine through the double-lumen needle.

In FIG. 5, the needle 10 is shown in use with a typical hemodialysis unit schematically indicated at reference numeral 56. the needle is inserted into a vein or fistula with the penetrating tip 16 pointing generally in the direction of blood flow. The mast 54 can be rotated to position the blood inlet 26 within the fistula so that the inlet is not blocked by a vein wall. Once positioned as described, the blood inlet encourages blood to enter the intake lumen 30 in a direction transverse to the longitudinal axis of the shaft. The venous or treated blood is returned through the blood outlet 24 longitudinally and therefore in the direction of blood flow. This arrangement greatly reduces the possibility of recirculation of the arterial blood with the venous blood.

Construction of the dual-lumen fistula needle 10 in this manner provides a dual-lumen needle which minimizes trauma to patients when the needle is inserted, which minimizes recirculation of arterial and venous blood, and which has substantially equal venous and arterial flow rates. Furthermore, by employing a separately manufactured center septum 28, which is chemically bonded to the inner surface 20 of the shaft, manufacture of the needle is greatly facilitated.

Other variations and embodiments of the needle, which utilize a separate center septum, a tapering shaft, and a transversely oriented blood inlet and outlet achieving substantially equal venous and arterial flow rates, are contemplated. Therefore, the scope of the invention is not to be limited to the above description, but is to be determined by the scope of the claims which follow.

We claim:

1. A dual-lumen fistula needle, comprising:
   a longitudinally extending cylindrical shaft having a smooth outer surface, a base, a distal end, and an inner surface defining a fluid conduit, a portion of the shaft being symmetrically tapered about the longitudinal axis of the shaft to form a neck having a gradually decreasing diameter;
   a penetrating tip at the distal end defining a blood outlet to communicate with the fluid conduit so that blood can exit the fluid conduit longitudinally;
   a blood inlet formed in the neck such that blood can enter the fluid conduit in a direction which is transverse to the longitudinal axis of the shaft; and
   a center septum within the shaft having a first rectangular portion defining a plane containing the longitudinal axis, and extending from the base to the beginning of the neck and a second, tapered portion bent out of the plane and extending into the neck, the taper on the second portion corresponding to the taper of the neck so that the width of the septum corresponds to the width of the inner surface, said septum dividing the fluid conduit into a blood intake lumen communicating with the blood inlet and a blood return lumen communicating with the blood outlet.

2. The needle of claim 1 wherein the distance between the smooth outer surface and the inner surface is substantially constant along the longitudinal axis of the shaft so that the cross-sectional area of the blood intake lumen is substantially equal to the cross-sectional area of the blood return lumen.

3. The needle of claim 2 wherein the areas defined by the blood inlet and the blood outlet are at least as large as the cross-sectional areas of the blood intake lumen and blood return lumen, respectively.

4. The needle of claim 3 wherein the length of the blood intake lumen is substantially equal to the length of the blood return lumen so that the flow rates of the lumens are substantially the same to prevent aeration of blood.

5. The needle of claim 1 including a chemical bond between the center septum and the inner surface of the shaft.

6. The needle of claim 1 wherein the inner surface is smooth to prevent turbulence in blood flow within the needle.

7. The needle of claim 1 wherein the center septum extends beyond the base of the shaft.

8. The needle of claim 7, including means for connecting the blood intake lumen and the blood return lumen with a hemodialysis unit.

9. The needle of claim 8, including a hemodialysis unit wherein the needle is operatively connected with the hemodialysis unit.

10. A dual-lumen fistula needle made by the process conprising the following steps:
symmetrically tapering a portion of a longitudinally extending cylindrical shaft having a base, a distal end and an inner surface defining a fluid conduit about the longitudinal axis of the shaft to form a neck having a gradually decreasing diameter;
forming a blood inlet in the neck;
forming a penetrating tip at the distal end to define a blood outlet;
applying a compressive force to the shaft along a first diameter sufficient to resiliently expand the shaft along a second diameter perpendicular to the first diameter;
inserting a center septum into the shaft, said septum having a first rectangular portion and a second, tapered portion bent out of the plane of the first portion, said septum being inserted into the shaft through the base so that the first rectangular portion is aligned with the expanded second diameter until the second tapered portion is seated against the tapered inner surface of the neck; and
releasing the compressive force so that the shaft returns to its original shape.

11. The dual-lumen fistula needle made by the process of claim 10, further comprising the step of applying a bonding agent to the edges of the septum to bond the septum to the inner surface of the shaft to divide the fluid conduit into a blood intake lumen communicating with the blood inlet and a blood return lumen communicating with the blood outlet.

12. The dual-lumen fistula needle made by the process of claim 11 wherein the bonding agent has a low viscosity and wherein the bonding agent is applied to the septum through the blood inlet so that the bonding agent is drawn along the edges of the septum by capillary action.

13. a dual-lumen fistula needle, comprising:
a longitudinally extending cylindrical shaft having a smooth outer surface, a base, a distal end, and an inner surface defining a fluid conduit, a portion of the shaft being symmetrically tapered about the longitudinal axis of the shaft to form a neck having a gradually decreasing diameter, the shaft also having a substantially constant wall thickness defined by the distance between the inner and outer surfaces;
a penetrating tip at the distal end defining a blood outlet to communicate with the fluid conduit so that blood can exit the fluid conduit longitudinally;
a blood inlet formed in the neck such that blood can enter the fluid conduit in a direction which is transverse to the longitudinal axis of the shaft; and
a center septum extending within the shaft from its base to the beginning of its neck, said septum having a first rectangular portion defining a plane containing the longitudinal axis, and a second tapered portion bent out of the plane and extending into the neck, the taper on the second portion corresponding to the taper of the neck so that the width of the septum corresponds to the transverse dimension of the inner surface, said septum dividing the fluid conduit into a blood intake lumen communicating with the blood inlet and a blood return lumen communicating with the blood outlet wherein the cross-sectional area of the blood intake lumen is substantially equal to the cross-sectional area of the blood return lumen.

* * * * *